(12) United States Patent
Milstein et al.

(10) Patent No.: US 8,178,723 B2
(45) Date of Patent: May 15, 2012

(54) PROCESS FOR PREPARING AMIDES FROM ALCOHOLS AND AMINES

(75) Inventors: David Milstein, Rehovot (IL); Chidambaram Gunanathan, Tamil Nadu (IN); Yehoshua Ben-David, Givatayim (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 525 days.

(21) Appl. No.: 12/260,936

(22) Filed: Oct. 29, 2008

(65) Prior Publication Data

US 2009/0112005 A1 Apr. 30, 2009

Related U.S. Application Data

(60) Provisional application No. 60/983,584, filed on Oct. 30, 2007.

(51) Int. Cl.
*C07C 231/10* (2006.01)
(52) U.S. Cl. ........................................... 564/123; 546/2
(58) Field of Classification Search .................. 564/123; 546/2
See application file for complete search history.

(56) References Cited

OTHER PUBLICATIONS

Abbenhuis, Rob A. T. M. et al., (1998) Ruthenium-Complex-Catalyzed N-(Cyclo)alkylation of Aromatic Amines with Diols. Selective Synthesis of N-(ω-Hydroxyalkyl)anilines of Type PhNH(CH$_2$)$n$OH and of Some Bioactive Arylpiperazines. J. Org. Chem. 63(13):4282-4290.
Ben-Ari, Eyal et al., (2006) Metal-Ligand Cooperation in C—H and H$_2$ Activation by an Electron-Rich PNP Ir(I) System: Facile Ligand Dearomatization-Aromatization as Key Steps. J. Am. Chem. Soc. 128(48):15390-15391 Epub Nov. 11, 2006.
Bray, Brian L. (2003) Large-scale manufacture of peptide therapeutics by chemical synthesis. Nat. Rev. Drug Discovery 2(7):587-93.
Cassidy, Michael P. et al., (2006) Practical Synthesis of Amides from In Situ Generated Copper(I) Acetylides and Sulfonyl Azides. Angew. Chem. Int. Ed. 45(19):3154-3157 Epub Mar. 29, 2006.
Chan, Wing-Kei et al., (2006) Oxidative amide synthesis and N-terminal alpha-amino group ligation of peptides in aqueous medium. J. Am. Chem. Soc. 128(46):14796-14797.
Cho, Seung Hwan et al., (2005) Copper-catalyzed hydrative amide synthesis with terminal alkyne, sulfonyl azide, and water. J. Am. Chem. Soc. 127(46):16046-16047.
Cobley, Christopher J. et al., (2000) Platinum catalysed hydrolytic amidation of unactivated nitriles. Tetrahedron Lett. 41(14):2467-2470.

Fujita, Ken-Ichi et al., (2004) Synthesis of five-, six-, and seven-membered ring lactams by CpRh complex-catalyzed oxidative N-heterocyclization of amino alcohols. Org. Lett. 6(16):2785-2788.
Hamid, Malai Haniti S. A. and Williams, Jonathan M. J. (2007) Ruthenium catalysed N-alkylation of amines with alcohols. Chem. Commun. 2007(7):725-727.
Murahashi, Shun-Ichi et al., (1986) Ruthenium-catalyzed hydration of nitriles with amines. A novel, facile route to amides and polyamides. J. Am. Chem. Soc. 108(14):7846-7847.
Murahashi, Shun-Ichi et al., (1992) Ruthenium-catalyzed hydration of nitriles and transformation of .delta.-keto nitriles to ene-lactams. J. Org. Chem. 57(9):2521-2523.
Naota, Takeshi and Murahashi, Shun-Ichi (1991) Ruthenium-Catalyzed Transformations of Amino Alcohols to Lactams. Synlett 1991(10):693-694.
Owston, N. A. et al., (2007) Iridium-catalyzed conversion of alcohols into amides via oximes. Org. Lett. 9(1):73-75 Epub Dec. 6, 2007.
Rannard, Steve P. and Davis, Nicola J. (2000) The selective reaction of primary amines with carbonyl imidazole containing compounds: selective amide and carbamate synthesis. Org. Lett. 2(14):2117-2120 Epub Jun. 17, 2000.
Tamaru, Yoshinao et al., (1983) Direct Oxidative Transformation of Aldehydes to Amides by Palladium Catalysis. Synthesis 6:474-476.
Tillack, Annegret et al., (2001) Catalytic Amination of Aldehydes to Amides. Eur. J. Org. Chem. 2001(3):523-528 Epub Jan. 16, 2001.
Watanabe, Yoshihisa et al., (1984) Ruthenium-catalyzed N-alkylation and N-benzylation of aminoarenes with alcohols. J. Org. Chem. 49(18):3359-3363.
Williams, J. C. and McDermott, A. E. (1998) Variable NMR Spin-Lattice Relaxation Times in Secondary Amides: Effect of Ramachandran Angles on the Librational Dynamics. J. Phys. Chem. 102:6248-6259.
Zhang, Jing et al., (2004) Electron-Rich, Bulky Ruthenium PNP-Type Complexes. Acceptorless Catalytic Alcohol Dehydrogenation. Organometallics 23(17):4026-4033 Epub Jul. 16, 2004.
Zhang, Jing et al., (2005) Facile conversion of alcohols into esters and dihydrogen catalyzed by new ruthenium complexes. J. Am. Chem. Soc. 127(31):10840-10841.
Zhang, Jing et al., (2006) Efficient Homogeneous Catalytic Hydrogenation of Esters to Alcohols. Angew. Chem. Int. Ed. 45(7):1113-1115 Epub Jan. 3, 2006.
Zhang, Jing et al., (2007) Electron-rich, bulky PNN-type ruthenium complexes: synthesis, characterization and catalysis of alcohol dehydrogenation. Dalton. Trans.7(1):107-113 Epub Nov. 6, 2007.

*Primary Examiner* — David K O Dell
(74) *Attorney, Agent, or Firm* — Winston & Strawn LLP (57) ABSTRACT

The present invention provides a process for preparing amides, by reacting a primary amine and a primary alcohol in the presence of a Ruthenium catalyst, to generate the amide and molecular hydrogen. According to the process of the invention, primary amines are directly acylated by equimolar amounts of alcohols to produce amides and molecular hydrogen (the only byproduct) in high yields and high turnover numbers. This reaction is catalyzed by a Ruthenium complex, which is preferably based on a dearomatized PNN-type ligand of formula A1 or precursors thereof of formulae A2 or A3. Use of diamines in the reaction leads to bis-amides, whereas with a mixed primary/secondary amine substrate, chemoselective acylation of the primary amine group occurs.

23 Claims, 2 Drawing Sheets

PROCESS FOR PREPARING AMIDES FROM ALCOHOLS AND AMINES

This application claims the benefit of U.S. provisional application No. 60/983,584 filed Oct. 30, 2007, the entire content of which is expressly incorporated herein by reference thereto.

FIELD OF THE INVENTION

The present invention relates to a process of preparing amides by reacting alcohols with amines in the presences of Ruthenium catalysts.

BACKGROUND OF THE INVENTION

Amide formation is a fundamental reaction in chemical synthesis (1). The importance of amides in chemistry and biology is well recognized and has been studied extensively over the past century (2-4). Although several methods are known for the synthesis of amides, preparation under neutral conditions and without generation of waste is a challenging goal (1, 5). Synthesis of amides is mostly based on activated acid derivatives (acid chlorides, anhydrides) or rearrangement reactions induced by acid or base which often involve toxic chemical waste and tedious work-up (5). Transition-metal catalyzed conversion of nitrites into amides was reported (6, 7, 8). Catalytic acylation of amines by aldehydes in the presence of a stoichiometric amount of oxidant and a base is known (9, 10). Recently, oxidative amide synthesis was achieved from terminal alkynes (11). Cu(I) catalyzed reaction of sulfonyl azides with terminal alkynes is a facile method for the synthesis of sulfonyl amides (12, 13).

The applicants of the present invention recently reported the dehydrogenation of alcohols catalyzed by PNP— and PNN—Ru(II) hydride complexes (14). Whereas secondary alcohols lead to ketones (15, 16), primary alcohols are efficiently converted into esters and dihydrogen (14-16). The dearomatized PNN pincer complex 1 (FIG. 1) is particularly efficient (17); it catalyzes this process in high yields under neutral conditions, in the absence of acceptors or promoters.

Given the widespread importance of amides in biochemical and chemical systems, an efficient synthesis that avoids wasteful use of stoichiometric coupling regents or corrosive acidic and basic media is highly desirable.

SUMMARY OF THE INVENTION

The present invention provides a process for preparing amides, by reacting a primary amine and a primary alcohol in the presence of a Ruthenium catalyst, to generate the amide compound and molecular hydrogen. As contemplated herein, the inventors have discovered a novel process for preparing amides in which primary amines are directly acylated by equimolar amounts of alcohols to produce amides and molecular hydrogen (the only byproduct) in high yields and high turnover numbers. This reaction is catalyzed by a Ruthenium complex, which is preferably based on a dearomatized PNN-type ligand, requiring no base or acid promoters, or is based on an aromatized precursor of the dearomatized PNN-type ligand, with the optional use of one or more equivalents of a base. Use of primary diamines in the reaction leads to bis-amides, whereas with a mixed primary/secondary amine substrate, chemoselective acylation of the primary amine group occurs.

The process of the invention, i.e., the direct catalytic conversion of alcohols and amines into amides and dihydrogen is illustrated in equation 1. This novel, environmentally benign reaction (18-22), can be used to produce various amides from very simple substrates, with high atom economy and in some embodiments no stoichiometric activating agents, thus generating no waste. Although such a reaction is expected to be thermodynamically uphill, it is contemplated that the liberated hydrogen gas will shift the equilibrium and will drive the reaction.

wherein $R^1$ and $R^2$ can be the same or different from each other.

The applicants of the present invention have unexpectedly discovered that Ruthenium complexes catalyze the reaction of alcohols with amines to form amides and $H_2$. In one embodiment, the Ruthenium catalyst is represented by any one of formulae A1, A2 or A3:

wherein
$L_1$ and $L_2$ are each independently selected from the group consisting of nucleophilic carbene (:$CR_2$), $PR_2$, $P(OR)_2$, $NR_2$, imine, SR, SH, S(=O)R, heteroaryl wherein the heteroatom is selected from nitrogen and sulfur, $AsR_2$, $SbR_2$ and an N-heterocyclic carbene represented by the structure:

wherein each of R, $R^1$, $R^2$ and $R^3$ is independently selected from the group consisting of alkyl, cycloalkyl, aryl, alkylaryl, heterocyclyl and heteroaryl;

$L_3$ is a mono-dentate two-electron donor selected from the group consisting of CO, $PR_3$, $P(OR)_3$, $NO^+$, $AsR_3$, $SbR_3$, $SR_2$, nitrile (RCN) and isonitrile (RNC) wherein R is as defined above;

$L_4$ is absent or is $L_3$;

Y and Z are each independently H or an anionic ligand such as halogen, OCOR, $OCOCF_3$, $OSO_2R$, $OSO_2CF_3$, CN, OH, OR, $NR_2$, RS or SH, wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support (e.g., silica) and a polymeric moiety (e.g., polystyrene); and anion represents a group bearing a single negative charge.

Embodiments wherein two substituents are connected to form a fused ring system (including fused aromatic structures), are also included within the scope of the invention.

In one embodiment, the Ruthenium catalyst is represented by the structure of formula A1:

In a particular embodiment of formula A1, the Ruthenium catalyst is represented by the structure of formula B1:

In another particular embodiment of formula A1, the Ruthenium catalyst is represented by the structure of formula C1:

wherein each of $R^a$, $R^b$, $R^c$ and $R^d$ is independently selected from the group consisting of alkyl, cycloalkyl, aryl, alkylaryl, heterocyclyl and heteroaryl.

Figure 1:
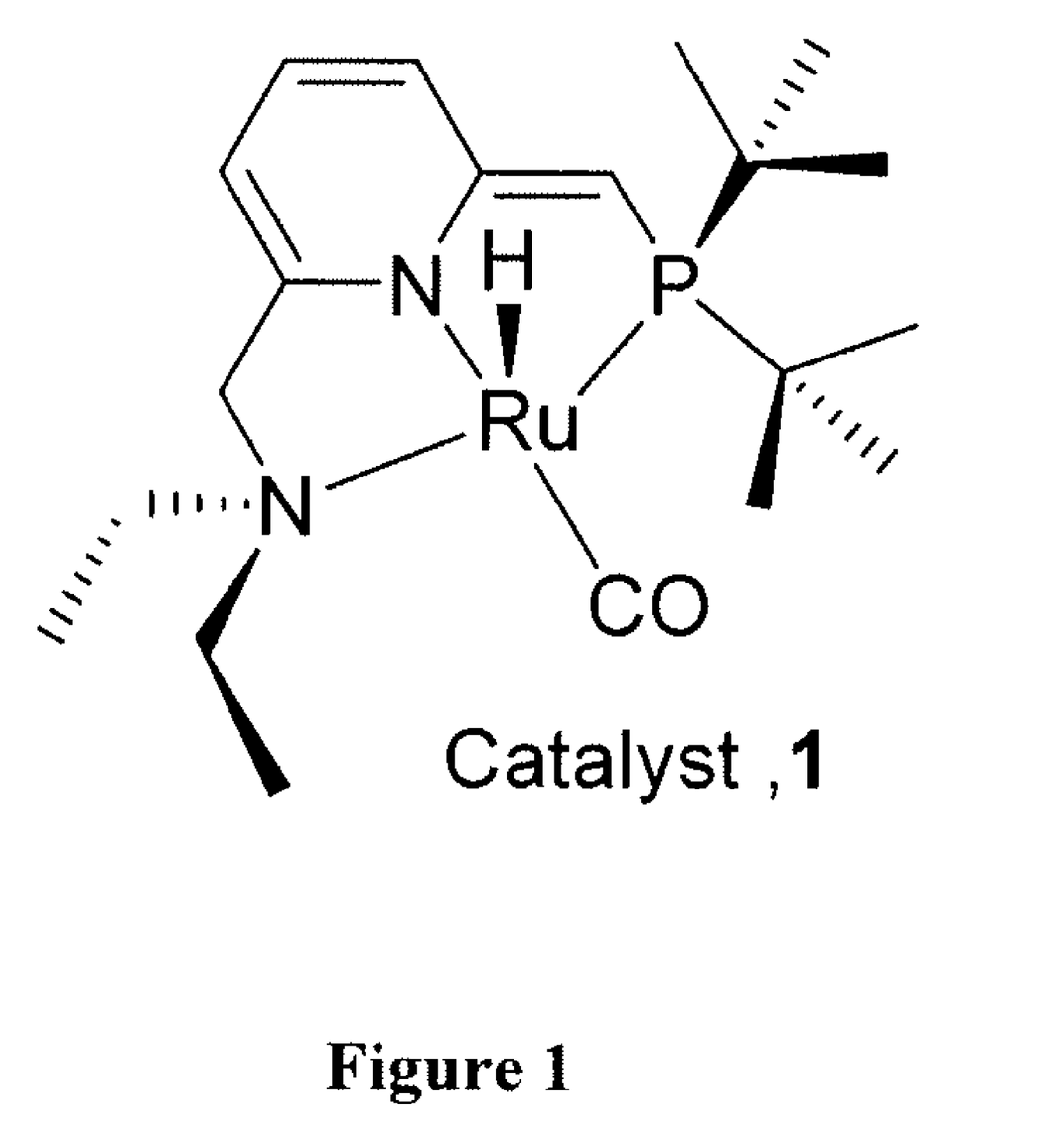
FIG. 1: shows the structure of dearomatized PNN pincer complex 1.
Figure 2:
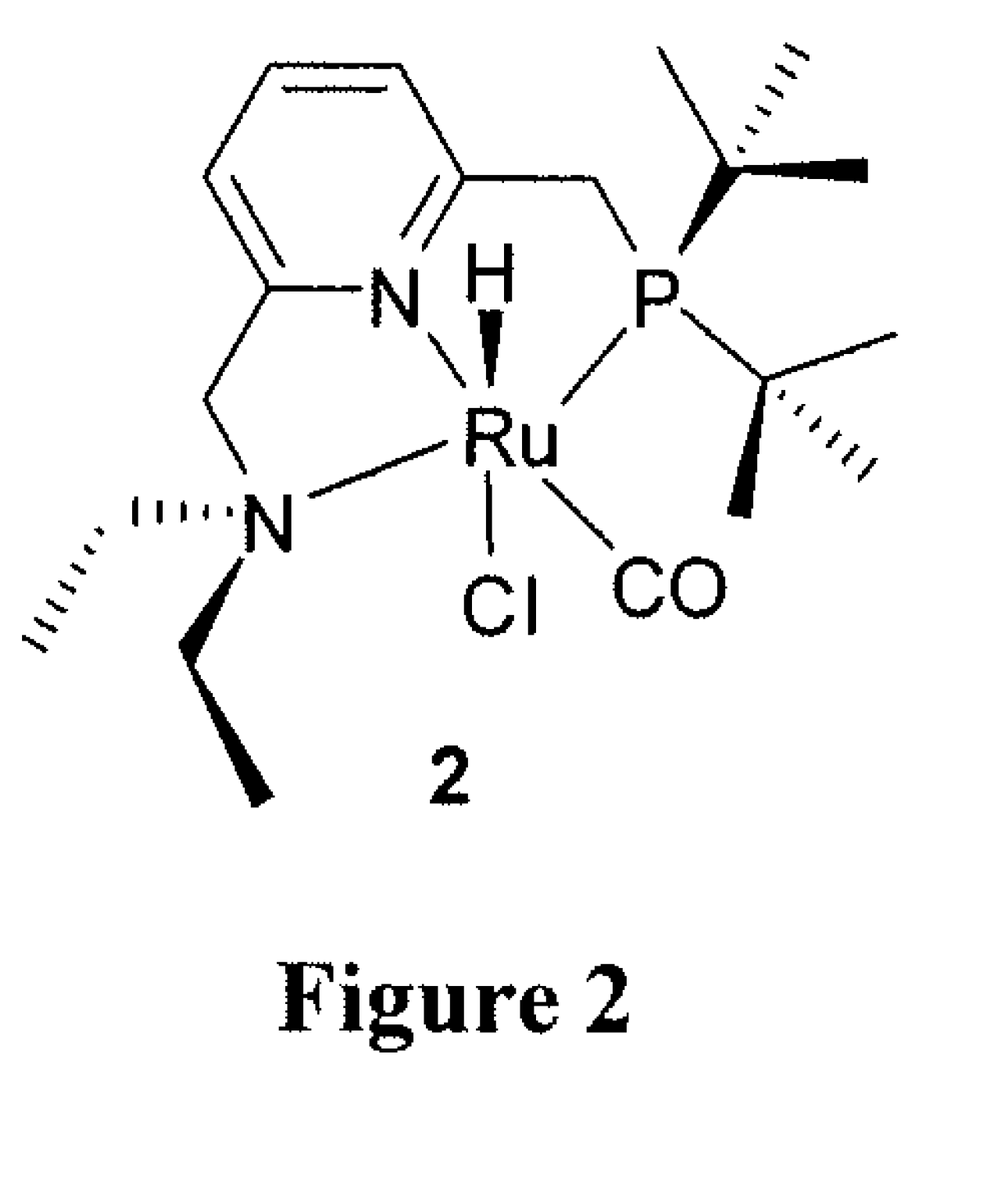
FIG. 2: shows the structure of an aromatized PNN pincer complex 2.

In one currently preferred embodiment, each of $R^a$ and $R^b$ is tert-butyl. In another currently preferred embodiment, each of $R^c$ and $R^d$ are ethyl. In a particularly preferred embodiment, the Ruthenium catalyst is represented by the structure of formula 1 (FIG. 1).

When the Ruthenium catalyst is a compound of formula A1, the process of the invention does not require the addition of any base or acid promoters.

In another embodiment of the present invention, the Ruthenium catalyst is represented by the structure of formula A2:

wherein Y and Z are each independently H or an anionic ligand such as halogen, OCOR, $OCOCF_3$, $OSO_2R$, $OSO_2CF_3$, CN, OH, OR, $NR_2$, SR or SH, and R is alkyl, cycloalkyl, aryl, alkylaryl, heterocyclyl or heteroaryl.

In one particular embodiment, Z is H and Y is other than H in formula A2. In accordance with this embodiment, the process of the invention is conducted in the presence of at least one equivalent of a base relative to the Ruthenium catalyst. In another particular embodiment, each of Z and Y is other than H in formula A2. In accordance with this embodiment, the process of the invention is conducted in the presence of at least two equivalents of a base relative to the Ruthenium catalyst. In another particular embodiment, Z and Y are both H in formula A2. In accordance with this embodiment, no base is required for the process of the invention.

In one embodiment of formula A2, the Ruthenium catalyst is represented by the structure of formula B2:

wherein Y is H or an anionic ligand such as halogen OCOR, $OCOCF_3$, $OSO_2R$, $OSO_2CF_3$, CN, OH, OR, $NR_2$, SR or SH, and R is alkyl, cycloalkyl, aryl, alkylaryl, heterocyclyl or heteroaryl.

In another particular embodiment of formula A2, the Ruthenium catalyst is represented by the following structure of formula C2:

C2 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, Y is halogen, such as chloro. A currently preferred catalyst is a Ruthenium catalyst is represented by the structure of formula 2:

2

In another embodiment of the present invention, the Ruthenium catalyst is represented by the structure of formula A3:

A3 wherein Z is H or an anionic ligand such as halogen, OCOR, OCOCF$_3$, OSO$_2$R, OSO$_2$CF$_3$, CN, OH, OR, NR$_2$, SH or SR, R is alkyl, cycloalkyl, aryl, alkylaryl, heterocyclyl or heteroaryl; and L$_4$ is either absent or is a mono-dentate two-electron donor selected from the group consisting of CO, PR$_3$, P(OR)$_3$, NO$^+$, AsR$_3$, SbR$_3$, SR$_2$, nitrile (RCN) and isonitrile (RNC) wherein R is as defined above.

In one particular embodiment, Z is H in formula A3. In accordance with this embodiment, the process is conducted in the presence of at least one equivalent of a base relative to the Ruthenium catalyst. In another particular embodiment, Z is other than H in formula A3. In accordance with this embodiment, the process is conducted in the presence of at least two equivalents of a base relative to the Ruthenium catalyst.

Compounds of formula A2 (of which Compound 2 is a representative) and formula A3 are precursors of compounds of formula A1. Additional exemplary precursors of the complexes of formula A1 include, but are not limited to:

plus at least one equivalent
of base relative to Ru
(eg alkoxide, hydroxide)

plus at least two equivalents
of base relative to Ru
(eg alkoxide, hydroxide)

It is understood that any one or more of the precursors can themselves function as catalysts in the process of the present invention.

A variety of primary alcohols can be used in the process of the invention. In one embodiment, the alcohol is represented by the formula $R^4CH_2OH$ wherein $R^4$ is selected from the group consisting of alkyl, alkoxyalkyl, cycloalkyl, aryl, alkylaryl, heterocyclyl and heteroaryl. In several exemplary embodiments, the alcohol is selected from the group consisting of ethanol, propanol, butanol, pentanol, hexanol, 2-methoxyethanol, and 2-methyl-1-butanol.

A variety of primary amines may be used in the process of the invention. In one embodiment, the amine is represented by the formula $R^5CH_2NH_2$ wherein $R^5$ is selected from the group consisting of alkyl, alkoxyalkyl, cycloalkyl, aryl, alkylaryl, heterocyclyl and heteroaryl. In several exemplary embodiments, the amine is selected from the group consisting of benzylamine, 1-(2-furyl)methylamine, aniline, pentylamine, 2-methylhexylamine, and cyclohexylamine.

In another embodiment, the process of the invention can also be applied to bis-acylation reactions with diamines. Upon reacting alcohols and diamines, the corresponding bis-amides are produced in high yields. In exemplary embodiments, the diamine is ethylenediamine or 1,6-diaminohexane.

Furthermore, it has been discovered that the amidation reactions have a high preference to primary amines. The high selectivity of the dehydrogenative amidation reaction to primary amine functionalities enables the direct bis-acylation of triamines such as diethylelentriamine to produce a diamide by reaction of the two primary amine functionalities.

The reaction between the amine and alcohol can be intermolecular (i.e., the amine and the alcohol are present in separate molecules). Alternatively, the reaction between the amine and alcohol can be intra-molecular, i.e., the amine and alcohol functionalities can be present in the same molecule, resulting in intra-molecular cyclization to generate a lactam.

Without wishing to be bound by any theory or mechanism, it is contemplated that the mechanism of the amidation process involves dehydrogenation of hemiaminal intermediates formed by reaction of an aldehyde intermediate with the amine.

BRIEF DESCRIPTION OF THE DRAWINGS

The present invention will be understood and appreciated more fully from the following detailed description taken in conjunction with the appended figures.

DETAILED DESCRIPTION OF THE PRESENT INVENTION

The present invention relates to a process for preparing an amide compound, comprising the step of reacting a primary amine and an alcohol in the presence of a Ruthenium catalyst, to generate the amide and molecular hydrogen. According to the invention, primary amines are directly acylated by equimolar amounts of alcohols to produce amides and molecular hydrogen in high yields and high turnover numbers.

This reaction is catalyzed by a Ruthenium complex, which is preferably based on a dearomatized PNN-type ligand, requiring no base or acid promoters, or is based on an aromatized precursor of the dearomatized PNN-type ligand, with the optional use of one or more equivalents of a base.

In one embodiment, the Ruthenium catalyst is represented by any one of formulae A1, A2 or A3:

wherein $L_1$ and $L_2$ are each independently selected from the group consisting of nucleophilic carbene (:$CR_2$), phosphide ($PR_2$), $P(OR)_2$, amine ($NR_2$), imine, sulfide (SR), thiolate (SH), sulfoxide (S(=O)R), heteroaryl wherein the heteroatom is selected from nitrogen and sulfur, arsine ($AsR_2$), stibine ($SbR_2$) and an N-heterocyclic carbene represented by the structure:

wherein each of R, $R^1$, $R^2$ and $R^3$ is independently selected from the group consisting of alkyl, cycloalkyl, aryl, alkylaryl, heterocyclyl and heteroaryl;

$L_3$ is a mono-dentate two-electron donor selected from the group consisting of CO, $PR_3$, $P(OR)_3$, $NO^+$, $AsR_3$, $SbR_3$, $SR_2$, nitrile (RCN) and isonitrile (RNC) wherein R is as defined above;

$L_4$ is absent or is $L_3$;

Y and Z are each independently H or an anionic ligand such as (but not limited to) halogen, OCOR, $OCOCF_3$, $OSO_2R$, $OSO_2CF_3$, CN, OH, OR, $NR_2$, RS or SH, wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support (e.g., silica) and a polymeric moiety (e.g., polystyrene); and anion represents a group bearing a single negative charge.

It is understood that when a phosphide group ($PR_2$) as defined above is attached to the carbon atom in the Ruthernium catalyst of the invention, it is designated a "phosphine" group.

It is further understood that Y and Z are not limited to the aforementioned groups, and that any other anionic ligands can be used and would be encompassed within the scope of the invention.

Embodiments wherein two substituents are connected to form a fused ring system (including fused aromatic structures), are also included within the scope of the invention.

In one embodiment, the Ruthenium catalyst is represented by the structure of formula A1:

In a particular embodiment of formula A1, the Ruthenium catalyst is represented by the structure of formula B1:

In another particular embodiment of formula A1, the catalyst is represented by the structure of formula C1:

C1 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, each of $R^a$ and $R^b$ is tert-butyl. In another currently preferred embodiment, each of $R^c$ and $R^d$ are ethyl. In a particularly preferred embodiment, the Ruthenium catalyst is represented by the structure of formula 1 (FIG. 1).

1

The Ruthenium catalyst of formula A1 is neutral. Furthermore, when a Ruthenium catalyst of formula A1 is used, the process of the invention does not require the addition of any base or acid promoters.

In another embodiment of the present invention, the Ruthenium catalyst is represented by the structure of formula A2:

A2 wherein Y and Z are each independently H or an anionic ligand such as (but not limited to) halogen, OCOR, OCOCF$_3$, OSO$_2$R, OSO$_2$CF$_3$, CN, OH, OR, NR$_2$, SR or SH, and R is alkyl, cycloalkyl, aryl, alkylaryl, heterocyclyl or heteroaryl.

In one particular embodiment, Z is H and Y is other than H in formula A2. In accordance with this embodiment, the process of the invention is conducted in the presence of at least one equivalent of a base relative to the Ruthenium catalyst. In another particular embodiment, each of Z and Y is other than H in formula A2. In accordance with this embodiment, the process of the invention is conducted in the presence of at least two equivalents of a base relative to the Ruthenium catalyst. In another particular embodiment, Z and Y are both H in formula A2. In accordance with this embodiment, no base is required for the process of the invention.

The Ruthenium catalyst of formula A2 is neutral.

In one embodiment of formula A2, the Ruthenium catalyst is represented by the structure of formula B2:

B2 wherein Y is independently H or an anionic ligand such as (but not limited to) halogen, OCOR, OCOCF$_3$, OSO$_2$R, OSO$_2$CF$_3$, CN, OH, OR, NR$_2$, SR or SH, and R is alkyl, cycloalkyl, aryl, alkylaryl, heterocyclyl or heteroaryl.

In another particular embodiment of formula A2, the Ruthenium catalyst is represented by the following structure of formula C2:

C2 wherein each of $R^a$, $R^b$, $R^c$ and $R^d$ is independently selected from the group consisting of alkyl, cycloalkyl, aryl, alkylaryl, heterocyclyl and heteroaryl.

In one currently preferred embodiment, Y is halogen, such as chloro. A currently preferred catalyst is Ruthenium catalyst is represented by the structure of formula 2:

2

In another embodiment of the present invention, the Ruthenium catalyst is represented by the structure of formula A3:

A3 wherein Z is H or an anionic ligand such as (but not limited to) halogen, OCOR, OCOCF$_3$, OSO$_2$R, OSO$_2$CF$_3$, CN, OH, OR, NR$_2$, SR or SH wherein R is alkyl, cycloalkyl, aryl, alkylaryl, heterocyclyl or heteroaryl; and $L_4$ is either absent or is a mono-dentate two-electron donor selected from the group consisting of CO, PR$_3$, P(OR)$_3$, NO$^+$, AsR$_3$, SbR$_3$, SR$_2$, nitrile (RCN) and isonitrile (RNC) wherein R is as defined above.

In one particular embodiment, Z is H in formula A3. In accordance with this embodiment, the process is conducted in the presence of at least one equivalent of a base relative to the Ruthenium catalyst. In another particular embodiment, Z is other than H in formula A3. In accordance with this embodiment, the process is conducted in the presence of at least two equivalents of a base relative to the Ruthenium catalyst.

Compounds of formula A2 (of which Compound 2 is a representative) and formula A3 are precursors of compounds of formula A1. Additional exemplary precursors of the complexes of formula A1 include, but are not limited to:

plus at least one equivalent
of base relative to Ru
(eg alkoxide, hydroxide)

plus at least two equivalents
of base relative to Ru
(eg alkoxide, hydroxide)

It is understood that any one or more of the precursors can themselves function as catalysts in the process of the present invention.

Other suitable Ruthenium catalysts that can be used in the process of the invention are the catalysts disclosed by Zhang et al. (14-17, the contents of each of which are incorporated by reference herein.

It is understood that when the catalyst includes one or more chiral centers, all stereoisomers are included in the scope of this invention.

A variety of alcohols can be used in the process of the present invention. In one embodiment, the alcohol is represented by the formula R$^4$CH$_2$OH wherein R$^4$ is selected from the group consisting of alkyl, alkoxyalkyl, cycloalkyl, aryl, alkylaryl, heterocyclyl and heteroaryl. In several exemplary and non-limiting embodiments, the alcohol is selected from the group consisting of ethanol, propanol, butanol, pentanol, hexanol, 2-methoxyethanol, and 2-methyl-1-butanol.

A variety of amines can be used in the process of the present invention. In one embodiment, the amine is represented by the formula R$^5$CH$_2$NH$_2$ wherein R$^4$ is selected from the group consisting of alkyl, alkoxyalkyl, cycloalkyl, aryl, alkylaryl, heterocyclyl and heteroaryl In several exemplary and non-limiting embodiments, the amine is selected from the group consisting of benzylamine, 1-(2-furyl)methylamine, aniline, pentylamine, 2-methylhexylamine, and cyclohexylamine.

As used herein, the term alkyl, used alone or as part of another group, refers, in one embodiment, to a "C$_1$ to C$_{12}$ alkyl" and denotes linear and branched, saturated or unsaturated (e.g, alkenyl, alkynyl) groups, the latter only when the number of carbon atoms in the alkyl chain is greater than or equal to two, and can contain mixed structures. Preferred are alkyl groups containing from 1 to 6 carbon atoms (C$_1$ to C$_6$ alkyls). More preferred are alkyl groups containing from 1 to 4 carbon atoms (C$_1$ to C$_4$ alkyls). Examples of saturated alkyl groups include, but are not limited to, methyl, ethyl, n-propyl, isopropyl, n-butyl, iso-butyl, sec-butyl, tert-butyl, amyl, tert-amyl, hexyl, Examples of alkenyl groups include, but are not limited to, vinyl, allyl, butenyl and the like. Examples of alkynyl groups include, but are not limited to, ethynyl, propynyl and the like. Similarly, the term "C$_1$ to C$_{12}$ alkylene" denotes a bivalent radicals of 1 to 12 carbons.

The alkyl group can be unsubstituted, or substituted with one or more substituents selected from the group consisting of halogen, hydroxy, alkoxy, aryloxy, alkylaryloxy, heteroaryloxy, oxo, cycloalkyl, phenyl, heteroaryls, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, alkylthio, arylthio, or alkylsulfonyl groups. Any substituents can be unsubstituted or further substituted with any one of these aforementioned substituents. By way of illustration, an "alkoxyalkyl" is an alkyl that is substituted with an alkoxy group.

The term "cycloalkyl" used herein alone or as part of another group, refers to a "C$_3$ to C$_8$ cycloalkyl" and denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl. An alkylaryl group denotes an alkyl group bonded to an aryl group (e.g., benzyl).

The term "heteroaryl" used herein alone or as part of another group denotes a heteroaromatic system containing at least one heteroatom ring atom selected from nitrogen, sulfur and oxygen. The heteroaryl contains 5 or more ring atoms. The heteroaryl group can be monocyclic, bicyclic, tricyclic and the like. Also included in this expression are the benzoheterocyclic rings. If nitrogen is a ring atom, the present invention also contemplates the N-oxides of the nitrogen containing heteroaryls. Nonlimiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group denotes a five-membered to eight-membered rings that have 1 to 4 heteroatoms, such as oxygen, sulfur and/or nitrogen. These five-membered to eight-membered rings can be saturated, fully unsaturated or partially unsaturated. Non-limiting examples of heterocyclic rings include piperidinyl, piperidinyl, pyrrolidinyl pyrrolinyl, pyrazolinyl, pyrazolidinyl, piperidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. The heterocyclyl group can be unsubstituted or substituted through available atoms with one or more groups defined hereinabove for alkyl.

The inorganic support which is attached to the pyridine ring in formula A can be, for example, silica, silica gel, glass, glass fibers, titania, zirconia, alumina and nickel oxide.

The polymer which is attached to the pyridine ring in formula A can be, for example, selected from polyolefins, polyamides, polyethylene terephthalate, polyvinylchloride, polyvinylidenechloride, polystyrene, polymethracrylate, natural rubber, polyisoprene, butadiene-styrene random copolymers, butadiene acrylonitrile copolymers, polycarbonate, polyacetal, polyphenylenesulfide, cyclo-olefin copolymers, styrene-acrylonitrile copolymers, ABS, styrene-maleic anhydride copolymers, chloroprene polymers, isobutylene copolymers, polystyrene, polyethylene, polypropylene, and the like.

The term "anion" as used herein refers to any moiety or group bearing a negative charge. Examples of anionic moieties include, but are not limited to halogen (e.g., F, Cl, Br, I), $OCOR$, $OCOCF_3$, $OSO_2R$, $OSO_2CF_3$, $BF_4$, $PF_6$, $SbF_6$, $BR_4$, $ClO_4$, $AlCl_4$, $CN$, $OH$, $OR$ or $NR_2$ wherein R is selected from alkyl, cycloalkyl, aryl, alkylaryl, heterocyclyl and heteroaryl, wherein each of the alkyl, cycloalkyl, aryl, alkylaryl, heterocyclyl and heteroaryl is as defined above.

The reaction between the amine and alcohol can be inter-molecular (i.e., the amine and the alcohol are present in separate molecules). Alternatively, the reaction between the amine and alcohol can be intra-molecular, i.e., the amine and alcohol functionalities can be present in the same molecule, resulting in intra-molecular cyclization to generate a lactam.

Exemplary Processes:

A. Catalysis with Ruthenium Catalyst 1:

When a toluene solution of Ruthenium catalyst 1 (0.2 mol %) with 1:1 benzylamine and 1-hexanol was refluxed in a closed system for 6 h, 63% conversion of 1-hexanol to N-benzyl hexanamide was observed. Continuing the reaction up to 40 h resulted in a mixture of products. In order to facilitate formation of the product amide by hydrogen removal, 1-hexanol and benzyl amine were heated with 1 (0.1 mol %) under a flow of argon in refluxing toluene for 7 h. This setup resulted in the formation of N-benzyl hexanamide in 96% yield and a trace of N-benzyl-hexyl-1-amine (1%). Interestingly, no formation of hexyl hexanoate, which forms quantitatively in the absence of amine, was observed (Table 1, entry 1). Repeating the reaction with 1-pentanol under identical conditions led to selective direct amidation, providing N-benzyl pentanamide in 97% yield (Table 1, entry 2). 2-Methoxyethanol underwent clean dehydrogenative acylation by reaction with the primary amines benzylamine, pentylamine, and cyclohexylamine to give methoxy acetylated amides in almost quantitative yields (entries 3, 8, and 10).

TABLE 1

Direct dehydrogenative acylation of amines with alcohols catalyzed by the ruthenium complex 1. Catalyst 1 (0.01 mmol), alcohol (10 mmol), amine (10 mmol), and toluene (3 mL) were refluxed under Argon flow (23). Conversion of alcohols was 100% (by GC analysis).

$$R^1CH_2OH + R^2-NH_2 \xrightarrow[\text{Toluene, Reflux, } -2H_2]{1\ (0.1\ \text{mol }\%), \Delta} R^2NHCOR^1$$

| Entry | $R^1CH_2OH$ | $R^2NH_2$ | Time (h) | Amides | Yield* (%) |
|---|---|---|---|---|---|
| 1 | pentyl-CH₂OH | Ph-CH₂-NH₂ | 7 | PhCH₂NHC(O)-pentyl | 96 |
| 2 | butyl-CH₂OH | Ph-CH₂-NH₂ | 7 | PhCH₂NHC(O)-butyl | 97 |
| 3 | MeOCH₂CH₂OH | Ph-CH₂-NH₂ | 9 | PhCH₂NHC(O)CH₂OMe | 99 |
| 4 | (CH₃)₂CHCH₂OH | Ph-CH₂-NH₂ | 12 | PhCH₂NHC(O)CH(CH₃)CH₂CH₃ | 70† |

TABLE 1-continued

Direct dehydrogenative acylation of amines with alcohols catalyzed by the ruthenium complex 1. Catalyst 1 (0.01 mmol), alcohol (10 mmol), amine (10 mmol), and toluene (3 mL) were refluxed under Argon flow (23). Conversion of alcohols was 100% (by GC analysis).

$$R^1CH_2OH + R^2-NH_2 \xrightarrow[\text{Toluene, Reflux, } -2H_2]{1\ (0.1\ \text{mol \%}),\ \Delta} R^2NHCOR^1$$

| Entry | R¹CH₂OH | R²NH₂ | Time (h) | Amides | Yield* (%) |
|---|---|---|---|---|---|
| 5 | pentyl-CH₂OH | furfurylamine | 8 | N-furfuryl hexanamide | 78† |
| 6 | pentyl-CH₂OH | dibenzylamine (Ph-CH₂-NH-CH₂-Ph) | 8 | N,N-dibenzyl hexanamide | 0† |
| 7 | butyl-CH₂OH | aniline | 8 | N-phenyl pentanamide | 58† |
| 8 | 2-methoxyethanol | pentylamine | 8 | N-pentyl 2-methoxyacetamide | 99 |
| 9 | pentyl-CH₂OH | 2-methylpentylamine (sec) | 8 | N-(sec-methylpentyl) hexanamide | 72† |
| 10 | 2-methoxyethanol | cyclohexylamine | 8 | N-cyclohexyl 2-methoxyacetamide | 99 |

*Isolated yields.
†The remaining alcohol was converted into the corresponding ester.
In the reactions involving hexanol and pentanol, trace amount of the corresponding secondary amines were detected (GC-MS).

It has further been discovered that the amidation reactions are sensitive to steric hindrance at the α positions of either the alcohol or the amine. Thus, when 2-methyl-1-butanol reacted with benzyl amine, the corresponding amide was obtained in 70% yield, the rest of the alcohol being converted to the ester 2-methylbutyl 2-methylbutanoate (Table 1, entry 4). A similar pattern was also observed when 2-methyl hexamine reacted with hexanol, leading to 72% yield of the corresponding amide (Table 1, entry 9). 1-(2-furyl)methylamine provided 78% yield of amide when reacted with 1-hexanol (Table 1, entry 5). When aniline was subjected to acylation with 1-pentanol, the amide was obtained in 58% yield (Table 1, entry 5). The lower reactivity of aniline may be attributed to its lower nucleophilicity as compared with alkylamines. Secondary amines do not react. Thus, heating dibenzyl amine with 1-hexanol under the experimental conditions resulted in a quantitative yield of hexyl hexanoate (Table 1, entry 6).

The inventors also examined bis-acylation processes with diamines. Upon refluxing a slight excess of a primary alcohol and catalyst 1 with diamines (500 equiv relative to 1) in toluene under argon, bis-amides were produced in high yields. Thus, reaction of 2-methoxyethanol with ethylene diamine, and 1-hexanol with 1,6-hexamethylene diamine resulted in quantitative yields of the corresponding bis-amides (Table 2, entries 1,3). The high selectivity of the dehydrogenative amidation reaction to primary amine functionalities enabled the direct bis-acylation of diethylenetriamine with 1-hexanol to provide the bis-amide in 88% yield without the need to protect the secondary amine functionality (Table 2, entry 2).

TABLE 2

Bis-acylation of diamines with alcohols catalyzed by 1. Catalyst 1 (0.01 mmol), alcohol (10.5 mmol), diamine (5 mmol), and toluene (5 mL) were refluxed under Ar flow (23).

| Entry | Diamine | Time (h) | Bis-amide | Yield (%) |
|---|---|---|---|---|
| 1 | Ethylenediamine | 9 |  | 99 |
| 2 | Diethylenetriamine | 8 |  | 88 |
| 3 | 1,6-Diaminohexane | 9 |  | 95 |

Though not wishing to be bound by any particular mechanism or theory, it is contemplated that the direct acylation of alcohols to amides with $H_2$ liberation may in principle proceed in two ways as shown in Scheme 1: (a) dehydrogenation of the alcohol to the aldehyde followed by its reaction with a primary amine to form a hemiaminal that is subsequently dehydrogenated to the amide; or (b) formation of a hemiacetal from the aldehyde and alcohol, followed by its dehydrogenation to the ester (14) which reacts with the amine to form the amide (24). The latter possibility is less likely to occur because refluxing a toluene solution of hexyl hexanoate (1.25 mmol) and benzyl amine (2.5 mmol) under argon for 8 h, either in the presence or absence of catalyst 1, resulted in no N-benzylhexanamide. Thus, it is contemplated that the reaction proceeds via the hemiaminal pathway.

Scheme 1

On the basis of the above results and the known chemistry of PNN-type pincer complexes (25), the mechanism depicted in Scheme 2 is tentatively proposed. Following a catalytic cycle for dehydrogenation of the alcohol to the corresponding aldehyde, reaction with the amine can form the hemiaminal B, which upon reaction with 1 can lead to the aromatic intermediate C. β-H elimination from C can form the observed product amide and generate the known (14,18) trans Ru dihydride complex 2. Elimination of dihydrogen from 2 (14,18) would regenerate catalyst 1, completing the catalytic cycle. Interestingly, the dehydrogenation of the hemiaminal B to the amide prevails relative to the expected facile water elimination to give an imine, which on hydrogenation would provide the secondary amine (26-28), observed only in trace amounts.

It is apparent to a person of skill in the art that the mechanism by which the reaction takes imposes no limitations on the scope of the invention.

B. Catalysis with Ruthenium Catalyst 2:

Complex RuH(Cl)(CO)(PNN) (PNN=[2-(di-tert-butylphosphinomethyl)-6-diethylaminomethyl)pyridine] (0.01 mmol), 1-hexanol (1.02 g, 10 mmol), Benzyl amine (1.07 g, 10 mmol) and toluene (3 mL) were taken in a Schlenk flask under an atmosphere of nitrogen. To the above mixture was added the base potassium-$^t$butoxide (1.1 mg, 0.01 mmol). The reaction mixture was pale yellow in color. Then, the flask was equipped with a condenser and the solution was refluxed with stirring under argon for 12 hrs. The color of the reaction mixture became brown. After cooling to room temperature, the consumption of starting materials was checked by GC using a Carboxen 1000 column on a HP 690 series GC system (100% conversion of alcohol was observed). Then, the solvent was evaporated in vacuum to obtain a white solid. The solid obtained was washed with hexane and dried in vacuum for 2-3 hrs.

Wt of the product N-benzylhexanoamide: 1.94 g Yield: 93.7%

MP: 55° C.

These results highlight the substantial scope for the preparation of the fundamental amide motif by direct acylation of amines with alcohols, a clear departure from the conventional synthetic procedures.

The disclosures of all cited references are incorporated by reference as if fully set forth herein.

EXPERIMENTAL DETAILS SECTION

General Experimental: All experiments with metal complexes and phosphine ligands were carried out under an atmosphere of purified nitrogen in a Vacuum Atmospheres glove box equipped with a MO 40-2 inert gas purifier or using standard Schlenk techniques. All solvents were reagent grade or better. All non-deuterated solvents were refluxed over sodium/benzophenone ketyl and distilled under argon atmosphere. Deuterated solvents were used as received. All solvents were degassed with argon and kept in the glove box over 4 Å molecular sieves. The ligand PNN (2-(di-tert-butylphosphinomethyl)-6-diethylaminomethyl)pyridine) and the catalyst 1 were prepared by reported methods (14). RuHCl(CO)(PPh$_3$)$_3$ was prepared according to a literature procedure (29). Satisfactory spectral and physical data were obtained for all amides.

Melting points are uncorrected. Thin layer chromatography (TLC) was performed on Merck 1.05554 aluminum sheets precoated with silica gel 60 F$_{254}$ and the spots visualized with UV light at 254 nm or under iodine. Column chromatography purifications were performed by flash chromatography using Merck silica gel 60 (0.063-0.200 mm). $^1$H, $^{13}$C and $^{31}$P NMR spectra were recorded at 500, 100, and 162 MHz, respectively, using a Bruker AMX-500 NMR spectrometer. $^1$H and $^{13}$C{$^1$H} NMR chemical shifts are reported in ppm downfield from tetramethylsilane. $^{31}$P NMR chemical shifts are reported in parts per million downfield from H$_3$PO$_4$ and referenced to an external 85% solution of phosphoric acid in D$_2$O. Abbreviations used in the NMR follow-up experiments: b, broad; s, singlet; d, doublet; t, triplet; q, quartet; m, multiplet. IR spectra were recorded on a Nicolet FT-IR spectrophotometer. Mass spectra were recorded on Micromass Platform LCZ 4000, using Electro Spray Ionization (ESI) mode.

Example 1

Representative Procedure for Catalytic Dehydrogenative Mono-Acylation of Primary Amines and Alcohols This example provides a typical procedure for the catalytic dehydrogenative mono-acylation of primary amines with alcohols (Table 1): Complex RuH(CO)(PNN*) 1 (0.01 mmol), an alcohol (10 mmol), an amine (10 mmol) and toluene (3 mL) were taken in a Schlenk flask under an atmosphere of purified nitrogen in a Vacuum Atmospheres glove box. The flask was equipped with a condenser and the solution was refluxed with stirring in an open system under argon for the specified time (Table 1). After cooling to room temperature, the consumption of starting materials was checked by GC using a Carboxen 1000 column on a HP 690 series GC system.

Purification of amides in entries 1-3, and 10: After completion of reaction, the reaction mixture was cooled and allowed to stand at room temperature, during which the product amides crystallized from the solution. The solution was decanted and the solids were washed with a mixture of hexane/toluene (1:1). The amides were dried under vacuum for overnight.

Purification of amides in entries 4-5 and 7-9: After completion of the reaction, the solvent was removed under vacuum and the resulting residue was purified by the column chromatography on silica gel using EtOAc/n-hexane.

Entry 6. After completion of reaction, the reaction mixture was cooled to room temperature and dibenzyl amine and hexyl hexanoate were determined by GC with mesitylene as an internal standard, using a Carboxen 1000 column on a HP 690 series GC system.

N-(2-furylmethyl)hexanoamide (entry 5): Colorless solid. mp 54-55° C. IR (KBr): 3296, 3065, 2953, 2930, 2871, 2870, 1634, 1545, 1456, 1426, 1383, 1150, 1079, 911, 728 cm$^{-1}$. $^1$H NMR (CDCl$_3$): 0.88 (t, $^3J_{H,H}$=7.0 Hz, 3H, CH$_3$), 1.24-1.35 (m, 4H, 2×CH$_2$), 1.63 (m, 2H, CH$_2$), 2.19 (t, $^3J_{H,H}$=7.9 Hz, 2H, COCH$_2$), 4.42 (d, $^3J_{H,H}$=5.3 Hz, 2H, NCH$_2$), 5.94 (bs, 1H, NH), 6.21 (d, $^3J_{H,H}$=2.5 Hz, 1H, CH), 6.31 (overlapping dd, $^3J_{H,H}$=3.0, 1.5 Hz, 1H, CH), 7.34 (s, 1H, OCH). $^{13}$C{$^1$H}NMR (CDCl$_3$): 13.87 (CH$_3$), 22.33 (CH$_2$), 25.28 (CH$_2$), 31.37 (CH$_2$), 36.35 (CH$_2$), 36.52 (CH$_2$), 107.25 (CH), 110.37 (CH), 142.04 (OCH), 151.44 (OCCH$_2$), 172.89 (NCO). Assignment of signals was confirmed by DEPT-135 NMR studies. MS (ESI) 218.24 (100%, (M+Na)$^+$). Anal. Calcd for C$_{11}$H$_{17}$NO$_2$: C, 67.66; H, 8.78; N, 7.17. Found: C, 67.92; H, 8.69; N, 7.24.

2-Methoxy-N-pentylacetamide (entry 8): Colorless oil. IR (neat): 3311, 2936, 1660, 1540.4, 1472.3 cm$^{-1}$. $^1$H NMR (CDCl$_3$): 0.90 (t, $^3J_{H,H}$=7.0 Hz, 3H, CH$_3$), 1.30-1.35 (m, 4H, 2×CH$_2$), 1.53 (quintet, $^3J_{H,H}$=7.0 Hz, 2H, CH$_2$), 3.28 (dt, $^3J_{H,H}$=7.0 Hz, 2H, NCH$_2$), 3.42 (s, 3H, OCH$_3$), 3.88 (s, 2H, OCH$_2$), 6.62 (bs, 1H, NH). $^{13}$C{$^1$H}NMR (CDCl$_3$): 13.68 (CH$_3$), 22.06 (CH$_2$), 28.77 (CH$_2$), 29.01 (CH$_2$), 38.49 (CH$_2$), 58.85 (OCH$_3$), 71.74 (CH$_2$), 169.08 (NCO). Assignment of signals was confirmed by DEPT-135 NMR studies. MS (ESI) 182.22 (100%, (M+Na)$^+$). HRMS calcd for C$_8$H$_{16}$NO$_2$: 158.1181. found 158.1176. Anal. Calcd for C$_8$H$_{17}$NO$_2$: C, 60.35; H, 10.76; N, 8.80. Found: C, 60.21; H, 10.83; N, 8.75.

N-(1-methylhexyl)hexanoamide (entry 9): Colorless oil. IR (neat): 3294, 2970, 2936, 2851, 1652, 1549, 1455 cm$^{-1}$. $^1$H NMR (CDCl$_3$): 0.84 (overlapping t, $^3J_{H,H}$=6.7 Hz, 6H, 2×CH$_3$), 1.08 (d, $^3J_{H,H}$=6.7 Hz, 3H, CH$_3$), 1.21-1.33 (m, 10H, 5×CH$_2$), 1.36-1.41 (m, 2H, CH$_2$), 1.60 (quintet, $^3J_{H,H}$=7.5 Hz, 2H, CH$_2$), 2.12 (t, $^3J_{H,H}$=7.5 Hz, 2H, CH$_2$), 3.93 (m, 1H), 5.83 (bs, 1H, NH). $^{13}$C{$^1$H}NMR (CDCl$_3$): 13.64 (CH$_3$), 13.7 (CH$_3$), 20.66 (CH$_3$), 22.18 (CH$_2$), 22.31 (CH$_2$), 25.43 (CH$_2$), 25.56 (CH$_2$), 31.24 (CH$_2$), 31.47 (CH$_2$), 36.57 (CH$_2$), 44.68 (CH), 172.29 (NCO). Assignment of signals was confirmed by DEPT-135 NMR studies. MS (ESI) 236.62 (100%, (M+Na)$^+$), 214.6 (13%, (M+1)$^+$). Anal. Calcd for C$_{13}$H$_{27}$NO: C, 73.18; H, 12.76; N, 6.56. Found: C, 72.89; H, 12.83; N, 6.53.

Typical procedure for the catalytic dehydrogenative bis-acylation of diamines with alcohols (Table 2): Complex 1 (0.01 mmol), an alcohol (10.5 mmol), an diamine (5 mmol), and toluene (5 mL) were placed in a Schlenk flask under an atmosphere of purified nitrogen in a Vacuum Atmospheres glove box. The flask was equipped with a condenser and the solution was refluxed with stirring in an open system under argon flow for the specified time (Table 2 in the paper). The reaction mixture was cooled to room temperature and the consumption of starting materials was checked by GC using a Carboxen 1000 column on a HP 690 series GC system. The reaction mixture was allowed to stand at room temperature and the bis-amides crystallized from the solution. The liquid was removed by decantation and the solids were washed with a mixture of dichoromethane/toluene (2:8). The resulting bis-amides were dried under vacuum overnight.

N,N'-ethane-1,2-diylbis(2-methoxyacetamide)(30) (entry 1): Colorless solid, mp 142-143° C. IR (CH$_2$Cl$_2$): 3294, 3063, 2987, 2460, 1685, 1429, 1285, 1131 cm$^{-1}$. $^1$H NMR (CDCl$_3$): 3.43 (s, 6H, OCH$_3$), 3.48 (s, 4H, 2×NCH$_2$), 3.91 (s, 4H, 2×OCH$_2$), 6.96 (bs, 2H, NH). $^{13}$C{$^1$H}NMR (CD$_3$OD): 39.59 (NCH$_2$), 59.55 (OCH$_3$), 72.59 (OCH$_2$), 172.99 (quat-C, NCO). Assignment of signals was confirmed by DEPT-135 NMR studies. MS (ESI) 227.58 (100%, (M+Na)$^+$). Anal. Calcd for C$_8$H$_{16}$N$_2$O$_4$: C, 47.05; H, 7.90; N, 13.72. Found: C, 47.23; H, 7.97; N, 13.62.

N,N'-(iminodiethane-2,1-diyl)dipentanoamide (entry 2): Colorless solid, mp 85-87° C. IR (neat): 3251, 3089, 2970, 2927, 2876, 1651, 1566, 1480, 1268, 1140 cm$^{-1}$. $^1$H NMR (CDCl$_3$): 0.92 (t, $^3J_{H,H}$=7.0 Hz, 6H, 2×CH$_3$), 1.36 (m, $^3J_{H,H}$=7.5, 7.0 Hz, 4H, 2×CH$_3$CH$_2$CH$_2$), 1.62 (overlapping two t, $^3J_{H,H}$=8.0, 7.5 Hz, 4H, 2×CH$_2$), 1.71 (s, 1H, NH), 2.20 (t, $^3J_{H,H}$=7.5 Hz, 4H, CH$_2$), 2.77 (t, $^3J_{H,H}$=6.0 Hz, 4H, CH$_2$), 3.35 (overlapping dt, $^3J_{H,H}$=6.0, 5.5 Hz, 4H), 5.99 (bs, 2H, CONH). $^{13}$C{$^1$H}NMR (CD$_3$OD): 14.15 (CH$_3$), 23.40 (CH$_2$), 29.10 (CH$_2$), 36.87 (CH$_2$), 39.84 (CH$_2$), 49.37 (CH$_2$), 176.51 (NCO). Assignment of signals was confirmed by DEPT-135 NMR studies. MS (ESI) 294.66 (100%, (M+Na)$^+$), 272.62 (43%, (M+1)$^+$). HRMS Calcd for C$_{14}$H$_{28}$N$_3$O$_2$: 270.2182. found 270.2177.

N,N'-hexane-1,6-diyldihexanoamide(31) (entry 3): Colorless solid. mp 140-142° C. IR (neat): 3311, 3063, 2945, 2868, 1642, 1549, 1481, 1438, 1379, 1226 cm$^{-1}$. $^1$H NMR (CDCl$_3$): 0.90 (t, $^3J_{H,H}$=7.0 Hz, 6H, 2×CH$_3$), 1.29-1.36 (m, 12H, 6×CH$_2$), 1.50 (m, 4H, 2×CH$_2$), 1.64 (quintet, $^3J_{H,H}$=7.0 Hz, 4H, 2×CH$_2$), 2.17 (t, $^3J_{H,H}$=7.5 Hz, 4H, 2×CH$_2$), 3.25 (overlapping 2 triplets, $^3J_{H,H}$=7.0 Hz, 4H, 2×CH$_2$), 5.6 (bs, 2H, NH). $^{13}$C{$^1$H}NMR (CD$_3$OD): 14.32 (CH$_3$), 23.44 (CH$_2$), 26.82 (CH$_2$), 27.59 (CH$_2$), 30.35 (CH$_2$), 32.52 (CH$_2$), 37.11 (CH$_2$), 40.19 (CH$_2$), 176.19 (NCO). Assignment of signals was confirmed by DEPT-135 NMR studies. MS (ESI) 648.44 (38%, (2M+Na)+), 335.87 (100%, (M+Na)+). Anal. Calcd for $C_{18}H_{36}N_2O_2$: C, 69.18; H, 11.61; N, 8.96. Found: C, 69.39; H, 11.56; N, 8.91

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

REFERENCES AND NOTES

1. R. C. Larock, *Comprehensive Organic Transformations* (VCH, New York, ed. 2, 1999).
2. N, Sewald, H.-D. Jakubke, *Peptides. Chemistry and Biology* (Wiley-VCH, 2002).
3. A. Greenberg, C. M. Breneman, J. F. Liebman, *The Amide Linkage: Selected Structural Aspects in Chemistry, Biochemistry, and Material Science* (Wiley, New York, 2000).
3. M. B. Smith, J. March, *Advanced Organic Chemistry* (Wiley, New York, ed. 5, 2001).
4. B. L. Bray, *Nat. Rev.* 2, 587-93 (2003).
5. M. B. Smith, *Compendium of Organic Synthetic Methods* (Wiley, 2001), Vol. 9, Pp 100-116.
6. C. J. Cobley, M. van den Heuvel, A. Abbadi, J. G. de Vries, *Tetrahedron Lett.* 41, 2467-2470 (2000).
7. S.-I. Murahashi, T. Naota, E. Saito, *J. Am. Chem. Soc.* 108, 7846-7847 (1986).
8. S.-I. Murahashi, S. Sasao, E. Saito, T. Naota, *J. Org. Chem.* 57, 2521-2523 (1992).
9. Y. Tamaru, Y. Yamada, Z. Yoshida, *Synthesis* 1983, 474-476 (1983).
10. A. Tillack, I. Rudloff, M. Beller, *Eur. J. Org. Chem.* 2001, 523-528 (2001).
11. W.-K. Chan, C.-M, Ho, M.-K. Wong, C.-M. Che, *J. Am. Chem. Soc.* 128, 14796-14797 (2006).
12. S. H. Cho, E. J. Yoo, I. Bae, S. Chang, *J. Am. Chem. Soc.* 127, 16046-16047 (2005).
13. M. P. Cassidy, J. Raushel, V. V. Fokin, *Angew. Chem. Int. Ed.* 45, 3154-3157 (2006).
14. J. Zhang, G. Leitus, Y. Ben-David, D. Milstein, *J. Am. Chem. Soc.* 127, 10840-10841 (2005).
15. J. Zhang, M. Gandelman, L. J. W. Shimon, D. Milstein, *Dalton. Trans.* 2007, 107-113 (2007).
16. J. Zhang, M. Gandelman, L. J. W. Shimon, D. Milstein, *Organometallics* 23, 4026-4033 (2004).
17. J. Zhang, G. Leitus, Y. Ben-David, D. Milstein, *Angew. Chem. Int. Ed.* 45, 1113-1115 (2006).
18. M. Hudlický, *Oxidations in Organic Chemistry*, (ACS monograph 186, Washington D.C., 1990), Pp 114-155.
19. 1-Butanol was acylated with amines using stoichiometric amount of imidazole (via carbonyl imidazole). Reaction time and yield were not reported. S. P. Rannard, N. J. Davis, *Org. Lett.* 2, 2117-2120 (2000).
20. For a procedure based on 3 separate reactions, involving aldehyde synthesis by alcohol dehydrogenation, reaction of the aldehyde with hydroxylamine hydrochloride to form an oxime, and rearrangement of the oxime to an amine, see N. A. Owston, A. J. Parker, J. M. J. Williams, *Org. Lett.* 9, 73-75 (2007).
21. In the presence of an excess of a sacrificial hydrogen acceptor, ruthenium catalyzed lactamization of amino alcohols with a total of 16 turnovers was reported: T. Naota, S.-I. Murahashi, *Synlett* 1991, 693-694 (1991).
22. Rh-catalyzed lactamization of aryl amino alcohols in the presence of base and hydrogen acceptor with a total of 20 turnovers: K. Fujita, Y. Takahashi, M. Owaki, K. Yamamoto, R. Yamaguchi *Org. Lett.* 6, 2785-2788 (2004).
23. See *Science* Online (www.Sciencemag.org/feature/data/ xxxxxxx.shl) Material for detailed procedures.
24. Intermolecular formation of amides from ester and amines catalyzed by aluminium and tin reagents are known. M. B. Smith, *Compendium of Organic Synthetic Methods* (Wiley, 2001), Vol. 9, p 110.
25. E. Ben-Ari, G. Leitus, L. J. W. Shimon, D. Milstein, *J. Am. Chem. Soc.* 128, 15390-15391 (2006).
26. Ruthenium catalyzed alkylation of amines by alcohols was reported, see M. H. S. A. Hamid, J. M. J. Williams, *Chem. Commun.* 2007, 725-727 (2007).
27. Y. Watanabe, Y. Tsuji, H. Ige, Y. Ohsugi, T. Ohta, *J. Org. Chem.* 49, 3359-3363 (1984).
28. R. A. T. M. Abbenhuis, J. Boersma, G. van Koten, *J. Org. Chem.* 63, 4282-4290 (1998).
29. N. Ahmad, J. J. Levison, S. D. Robinson, M. F. Uttley, *Inorg. Synth.* 15, 45 (1974).
30. B. Horst, D. Lothar, F. Juergen, R. Siegfried, *Chem. Ber.* 95, 1832-1893 (1962).
31. J. C. Williams, A. E. McDermott, *J. Phys. Chem.* 102, 6248-6259 (1998).

What is claimed is:

1. A process for preparing an amide, comprising the step of reacting a primary amine and a primary alcohol in the presence of a Ruthenium catalyst represented by the structure of any one of formulae A1, A2 or A3:

A1

A2

A3 wherein $L_1$ is $NR_2$;

$L_2$ is selected from the group consisting of nucleophilic carbene (:$CR_2$), $PR_2$, $P(OR)_2$, $NR_2$, imine, SR, SH, S(=O)R, heteroaryl wherein the heteroatom is selected from nitrogen and sulfur, $AsR_2$, $SbR_2$ and an N-heterocyclic carbene represented by the structure:

wherein each of R, $R^1$, $R^2$ and $R^3$ are independently selected from the group consisting of alkyl, cycloalkyl, aryl, alkylaryl, heterocyclyl and heteroaryl;

$L_3$ is a mono-dentate two-electron donor selected from the group consisting of CO, $PR_3$, $P(OR)_3$, $NO^+$, $AsR_3$, $SbR_3$, $SR_2$, nitrile (RCN) and isonitrile (RNC) wherein R is as defined above;

$L_4$ is absent or is $L_3$;

Y and Z are each independently H or an anionic ligand selected from the group consisting of halogen, OCOR, $OCOCF_3$, $OSO_2R$, $OSO_2CF_3$, CN, OH, OR, $NR_2$,

RS and SH; wherein R is as defined above;

X represents zero, one, two or three substituents selected from the group consisting of alkyl, aryl, halogen, nitro, amide, ester, cyano, alkoxy, cycloalkyl, alkylaryl, heterocyclyl, heteroaryl, an inorganic support and a polymeric moiety; and anion represents a group bearing a single negative charge;

thereby generating the amide and molecular hydrogen, wherein the process is conducted either with (a) Ruthenium catalyst A1 in the absence of a base; or (b) Ruthenium catalyst A2 or A3 in the presence of one or two equivalents of base relative to the amount of the Ruthenium catalyst.

2. The process of claim 1, wherein the Ruthenium catalyst is represented by the structure of formula A1:

3. The process of claim 2, wherein the Ruthenium catalyst is represented by the structure of formula B1:

B1

4. The process of claim 3, wherein the Ruthenium catalyst is represented by the structure of formula C1:

C1 wherein each of $R^a$, $R^b$, $R^c$ and $R^d$ is independently selected from the group consisting of alkyl, cycloalkyl, aryl, alkylaryl, heterocyclyl and heteroaryl.

5. The process of claim 4, wherein the Ruthenium catalyst is represented by the structure of compound 1:

1

6. The process of claim 1, wherein the Ruthenium catalyst is represented by the structure of formula A2:

7. The process of claim 6, wherein Z is H and Y is other than H, and the process further comprises adding one equivalent of a base relative to the Ruthenium catalyst.

8. The process of claim 6, wherein each of Z and Y is other than H, and the process further comprises adding two equivalents of a base relative to the Ruthenium catalyst.

9. The process of claim 6, wherein Z and Y are both H.

10. The process of claim 6, wherein the Ruthenium catalyst is by the structure of formula B2:

B2

11. The process of claim 10, wherein the Ruthenium catalyst is represented by the structure of formula C2:

C2

12. The process of claim 11, wherein Y is halogen.

13. The process of claim 12, wherein the Ruthenium catalyst is represented by the structure of compound 2:

2

14. The process of claim 1, wherein the Ruthenium catalyst is represented by the structure of formula A3:

anion$^\ominus$.

15. The process of claim 14, wherein Z is H, and the process comprises adding one equivalent of a base relative to the Ruthenium catalyst.

16. The process of claim 14, wherein Z is other than H, and the process comprises adding two equivalents of a base relative to the Ruthenium catalyst.

17. The process of claim 1, wherein the alcohol is represented by the formula $R^4CH_2OH$ wherein $R^4$ is selected from the group consisting of alkyl, alkoxyalkyl, cycloalkyl, aryl, alkylaryl, heterocyclyl and heteroaryl.

18. The process of claim 17, wherein the alcohol is selected from the group consisting of ethanol, propanol, butanol, pentanol, hexanol, 2-methoxyethanol, and 2-methyl-1-butanol.

19. The process of claim 1, wherein the amine is represented by the formula $R^5CH_2NH_2$ wherein $R^5$ is selected from the group consisting of alkyl, alkoxyalkyl, cycloalkyl, aryl, alkylaryl, heterocyclyl and heteroaryl.

20. The process of claim 1, wherein the amine is a diamine, and the process results in a diamide.

21. The process of claim 19, wherein the amine is selected from the group consisting of benzylamine, 1-(2-furyl)methylamine, aniline, pentylamine, 2-methylhexylamine, cyclohexylamine, ethylenediamine, diethylenetriamine and 1,6-diaminohexane.

22. The process of claim 1, wherein the reaction between the amine and the alcohol is intramolecular, thereby forming a lactam.

23. The process of claim 1, wherein the reaction between the amine and the alcohol is intermolecular and the molecular hydrogen is the only byproduct of the reaction.

* * * * *

UNITED STATES PATENT AND TRADEMARK OFFICE
CERTIFICATE OF CORRECTION

PATENT NO. : 8,178,723 B2
APPLICATION NO. : 12/260936
DATED : May 15, 2012
INVENTOR(S) : Milstein et al.

It is certified that error appears in the above-identified patent and that said Letters Patent is hereby corrected as shown below:

Column 25:
Line 24, after "$NR_2$,", insert -- RS and SH; wherein R is as defined above; --.
Line 25, delete "RS and SH; wherein R is as defined above;"
Lines 45-54, delete formula A1 and insert the following:

Lines 58-65, please delete formula B1 and insert the following:

Column 26:
Lines 23-33, please delete compound 1 and insert the following:

Signed and Sealed this
Twenty-sixth Day of June, 2012

David J. Kappos
*Director of the United States Patent and Trademark Office*

Column 26 (continued):
Lines 38-44, please delete formula A2 and insert the following:

Lines 58-65, please delete formula B2 and insert the following:

Column 27:
Lines 4-12, please delete formula C2 and insert the following:

Lines 18-28, please delete compound 2 and insert the following:

Lines 33-43, please delete formula A3 and insert the following: